(12) United States Patent
Kleen et al.

(10) Patent No.: US 7,479,141 B2
(45) Date of Patent: Jan. 20, 2009

(54) ABLATION TIP CATHETER DEVICE WITH INTEGRATED IMAGING, ECG AND POSITIONING DEVICES

(75) Inventors: Martin Kleen, Neunkirchen (DE); Norbert Rahn, Forchheim (DE)

(73) Assignee: Siemens Aktiengesellschaft, Munich (DE)

( * ) Notice: Subject to any disclaimer, the term of this patent is extended or adjusted under 35 U.S.C. 154(b) by 514 days.

(21) Appl. No.: 10/992,181

(22) Filed: Nov. 18, 2004

(65) Prior Publication Data

US 2005/0148836 A1 Jul. 7, 2005

(30) Foreign Application Priority Data

Nov. 26, 2003 (DE) ................................ 103 55 275

(51) Int. Cl.
*A61B 18/18* (2006.01)
(52) U.S. Cl. ............................ 606/41; 607/122; 606/34
(58) Field of Classification Search .................. 606/41, 606/45, 49, 7, 13–16; 607/122
See application file for complete search history.

(56) References Cited

U.S. PATENT DOCUMENTS

| 5,056,503 | A | | 10/1991 | Nagasaki et al. | |
|---|---|---|---|---|---|
| 5,391,199 | A | * | 2/1995 | Ben-Haim | ................... 607/122 |
| 5,782,899 | A | * | 7/1998 | Imran | ........................ 607/122 |
| 5,954,665 | A | * | 9/1999 | Ben-Haim | ................... 600/515 |
| 6,047,218 | A | | 4/2000 | Whayne et al. | |
| 6,456,769 | B1 | * | 9/2002 | Furusawa et al. | ........... 385/117 |
| 6,690,963 | B2 | * | 2/2004 | Ben-Haim et al. | .......... 600/424 |

FOREIGN PATENT DOCUMENTS

DE 102 12 841 A1 10/2003

* cited by examiner

*Primary Examiner*—Michael Peffley

(57) ABSTRACT

Catheter device comprising a catheter (2), particularly an intravascular catheter, for insertion into an organ or vessel of the human or animal body, with a device for ablation of the adjacent organ tissue or vessel tissue using high-frequency currents in the region of the tip of the catheter, a device (3, 11, 12, 18, 19, 23, 24) being integrated for capturing images of the organ or vessel in the region of the tip of the catheter (10, 17, 22).

7 Claims, 1 Drawing Sheet

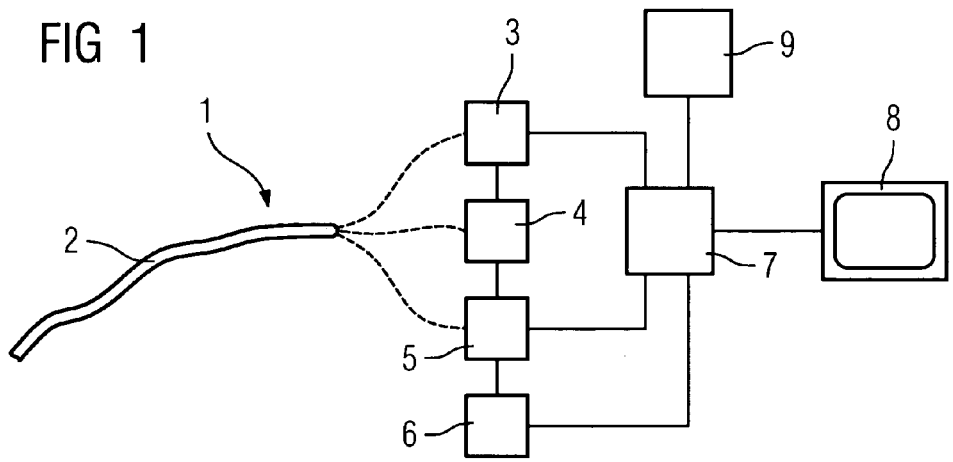
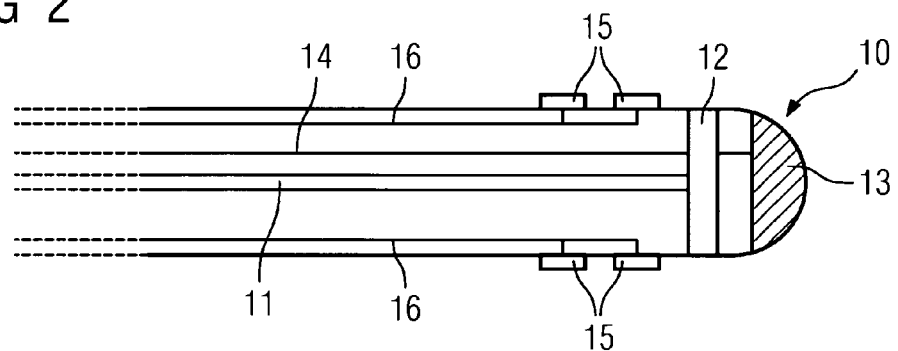
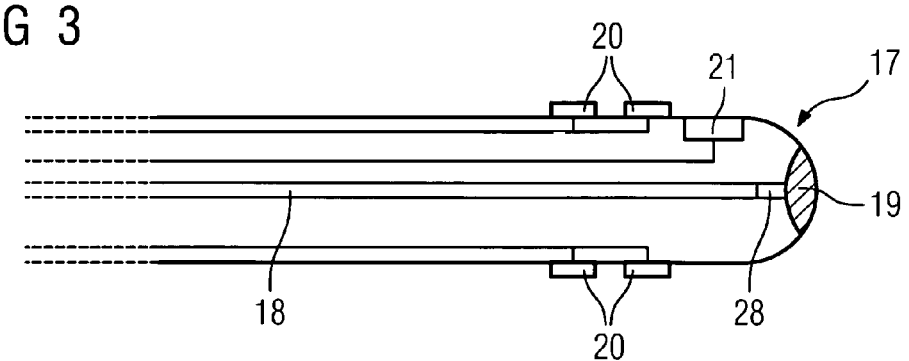
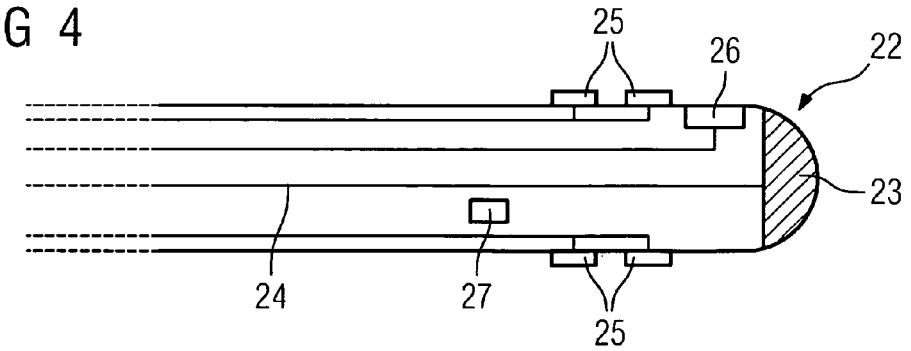

ABLATION TIP CATHETER DEVICE WITH INTEGRATED IMAGING, ECG AND POSITIONING DEVICES

CROSS REFERENCE TO RELATED APPLICATIONS

This application claims priority to the German application No. 10355275.8, filed Nov. 26, 2003 which is incorporated by reference herein in its entirety.

FIELD OF INVENTION

The invention relates to a catheter device comprising a catheter, in particular an intravascular catheter, for insertion into an organ or vessel of the human or animal body, with an ablation device comprising an ablation electrode arranged in the region of the tip of the catheter for ablation of the adjacent organ tissue or vessel tissue using high-frequency currents, an imaging device to capture images of the organ or vessel in the region of the tip of the catheter, as well as an ECG device to record an ECG comprising one or more electrodes provided in the area of the tip of the catheter to derive an ECG, as known for example from U.S. Pat. No. 6,047,218.

BACKGROUND OF INVENTION

Ablation catheters, i.e. catheters with a device for tissue ablation by necrotizing the tissue, are variously used, for example to treat arteriosclerosis, to treat vessel malformations, tumors, etc. Special importance is also attached here to the treatment of ventricular tachycardia or heart flutter. A heart attack often leaves scars, in particular in the ventricle, which negatively affect the stimulus conduction capability in the myocardium of the ventricle. Stimulus conduction capability is essential for the functioning of the heart, it being known that said functioning is based on very complex electrophysiological phenomena based on stimulus currents which are generated and routed via the ions of the heart muscle cells and via which contraction of the heart muscle is controlled. In the ventricle, in the region of the scars resulting from a heart attack, there is locally damaged cell tissue, the degree of damage diminishing toward the edge of the damaged tissue. Particularly in this region containing only partially functionally impaired cells there is a risk that stimulation current conduction is insufficient, resulting in a continuous pulse being emitted which can lead to an atrial flutter.

This "re-entry phenomenon" is mostly countered by selectively making scars in the region of the heart muscle by catheter ablation, in order to kill off completely the only partially damaged tissue in the region of the scars resulting from the heart attack, since dead tissue has no effect on stimulus current conduction. The scars produced by ablation are frequently positioned as a function of an electrophysiological determination of the site of the ablation.

Although catheter ablation generally takes place with X-ray monitoring, i.e. the doctor can identify the position of the ablation catheter in the heart from the X-ray image, he nevertheless has no information on the actual condition of the tissue in the treatment area and whether he is actually performing ablation at the place where it is required.

DE 102 12 841 A1 describes a catheter with an ablation facility, it being possible to detect the tip of the catheter using a position-recording device.

U.S. Pat. No. 5,056,503 discloses a very specifically designed endoscopy device which has a solid state capture element, i.e. an imaging element.

SUMMARY OF INVENTION

The invention is based on an object of specifying a catheter device which enables the doctor to obtain information from the treatment area in simple fashion, permitting safe and purposeful working.

This object is achieved by the claims.

The inventive proposed integration of an imaging device in the region of the tip of the catheter allows the doctor particularly advantageously to display the area under examination at high resolution, for example on a monitor, i.e. for example areas of scarred tissue or the delimitation thereof from healthy tissue, i.e. consequently to obtain an internal view of the heart, atrium, etc. Simultaneously he can undertake the ablation using the same catheter, i.e. necrotize the area of scared tissue displayed to him by imaging, using the high-frequency application.

Thus while working in the area under examination the doctor is given optical information directly on the area under examination at the same time as the possibility of ablation, without having to use an extra catheter or other medical instrument. In conjunction with the possibility of X-ray monitoring already known, the doctor can thus maneuver and work precisely in the area under examination without further action. The catheter device of course has means for power feed in order to carry out the ablation, integrated into the catheter in the form of thin feed lines. A data processing device is naturally also provided, which is used to process the image data captured, which can be captured in various forms. Finally it must be stated that it is not essential for the catheter to be flexible—it can also be a rigid device. The term "catheter" should also be understood to include for example a laparoscope, etc.

As described above, the invention provides for an imaging device to be integrated into the tip of the catheter. It is possible in this case to integrate an optical coherence tomography device. Such an optical coherence tomography device ("OCT" device) enables a high-resolution image of the area under examination to be displayed in real time. It is based in known fashion on the coherence principle. Two-dimensional sectional images are produced by beaming light into the object via the catheter and analyzing the reflected light. As with B-mode ultrasound, light is emitted and the reflection from the tissue or organ is analyzed to obtain information on the structures of the irradiated object. In coherence tomography deep information, i.e. the image information from the tissue or organ, is achieved using interferometry with a reference light beam of known run length. The length of the reference light beam is continuously changed. The interference occurring at the interferometer output relates to object points in the examination light beam, for which the lengths of reference beam and examination light beam are identical, calculated as far as the object in question. The light is beamed into the tissue using a thin light guide with a diameter of <1 mm, so optical coherence tomography can in particular be used wherever a thin catheter can be introduced.

Optical coherence tomography provides two-dimensional sectional images from the scan using the light beam emitted in the catheter, said beam rotating to create a local sectional image. This is therefore an annular image with a rotating light beam, predominantly a laser.

Optical coherence tomography is known per se and need not be described in greater detail. In all cases the thin light guide described, running to the tip of the catheter, must be provided in the catheter, as well as an interferometer via which the light is supplied, the reflected light is captured and the comparison with the reference light made.

As an alternative to using an OCT unit it is also conceivable to integrate an ultrasound device in the tip of the catheter. A miniaturized ultrasonic head is provided in the tip here, with the corresponding lines to emit the ultrasound signals and to derive the reflection signals likewise being routed through the catheter to a corresponding processing device outside.

As described, rotating light decoupling is generally used in the OCT device, a single light-conducting fiber being used. The light decoupling takes place laterally on the catheter, i.e. essentially perpendicular to the catheter's longitudinal axis. However, it is also conceivable to route a bundle of several individual fibers to the tip of the catheter and to place a collimator upstream of the individual fibers to ensure that the light emitted is reflected precisely to that fiber from which the light was emitted. This embodiment enables the OCT light to be coupled out and coupled in at the tip, i.e. in an extension of the catheter's longitudinal axis.

As described, the multifunctional catheter permits high-resolution images of the area under examination to be captured and ablation to be performed with the same device. It is particular expedient for ablation and imaging to be performed simultaneously, so that the doctor can see in situ where and how the ablation is being performed, i.e. he can continuously monitor the result of the treatment. The penetration depth of the additional ablation-induced lesion and the uninterrupted linearity of several adjacent linear lesions can likewise be displayed immediately after the ablation via the OCT or ultrasound unit.

A particularly advantageous embodiment according to the invention further provides for one or more electrodes in the region of the tip of the catheter to derive an ECG. Whereas when treating for example arteriosclerosis or vessel malformations, tumors, etc. the pathological area can readily be identified optically, i.e. it can be identified immediately without any further action via the imaging system, damaged tissue can only be located electrophysiologically in the case of ventricular tachycardia and similar illnesses. To this end, for example, the ventricle can be locally scanned using an ECG catheter, in order to take a local, surface ECG and to determine the position of the damaged tissue to be treated on the basis of the ECG signals received. These are therefore defects which are not optically visible and which can only be qualified and quantified electrophysiologically.

The inventive integration additionally of the ECG electrodes to derive the ECG particularly advantageously offers the opportunity, using the same instrument for example as part of a first optional step, to initially map the damaged ventricle using a suitable mapping system processing the ECG data received and on the basis of the result to record the electrophysiological disruption of stimulus conduction and to capture a spatial image of the heart to display an image of the electrophysiologically defined damaged areas. Such a mapping system is for example the CARTO system from Biosense-Webster, Diamondbar, Calif., USA. In each case it is possible—regardless of whether such mapping is performed—to check on the success of the necrotization and thus the elimination of disruption of stimulus conduction, since an intracardial ECG can also be derived simultaneously with the ablation and with the visualization, for example in the course of the OCT, and firstly the scarred tissue, i.e. the dead tissue, can be differentiated precisely from the healthy adjacent tissue electrophysiologically. Secondly, after necrotization of the scarred area the selectively eliminated stimulus conduction capability can be verified in these regions by taking the intracardial ECG. The corresponding supply lines for the ECG electrodes and the signal lines for the ECG signals are of course integrated into the catheter and a corresponding processing device is provided.

As described, the derivation of the ECG can advantageously be undertaken simultaneously with the ablation and/or imaging. If it is possible to undertake ECG mapping, an advantageous embodiment of the invention provides for the simultaneously captured image data and ECG data to be assigned to one another when imaging and ECG derivation are performed simultaneously. This marriage of data means that for each pathological location determined by the ECG the corresponding image, i.e. for example the corresponding OCT image, can be displayed. During mapping a relatively large region of the area under examination must as described be scanned point by point and the local ECG performed. If simultaneously with this the respective OCT or ultrasound image is already being taken, the data assignment according to the invention can take place immediately. Both data records are consequently referenced to one another.

According to a particularly advantageous development of the concept of the invention, provision can ultimately be made for one or more position sensors in the area of the tip of the catheter to enable the position and/or orientation of the tip of the catheter to be determined in a position recording coordinates system. The integration of the position recording facility is advantageous, since it provides information on the actual position of the catheter and thus also of the image data and ECG data captured. This information can expediently be used when on the basis of the knowledge of the spatial catheter position and orientation the data captured can for example be married with data from a previous magnetic resonance or computer tomography examination. This means that different data records can be recorded with one another on the basis of the known assignment rules by recording the different coordinates systems. However it is also expedient to record the position in the context of generating an ECG mapping.

BRIEF DESCRIPTION OF THE DRAWINGS

Further advantages, features and details of the invention emerge from the exemplary embodiment described below and on the basis of the drawings. These show:

FIG. 1 a device according to the invention together with ancillary units,

FIG. 2 an outline sketch of an enlarged view of a tip of the catheter of a first embodiment, FIG. 3 an outline sketch of an enlarged view of a tip of the catheter of a second embodiment, and FIG. 4 an outline sketch of an enlarged view of a tip of the catheter of a third embodiment.

DETAILED DESCRIPTION OF INVENTION

FIG. 1 shows a catheter device 1 according to the invention with the catheter 2. For operation, a series of ancillary units is assigned to this. Firstly this is a device 3 to record optically reproducible data from the area under examination, recorded via the tip of the catheter. For example, the device 3 is an interferometer as part of an optical coherence tomography device, which is dealt with further below. Alternatively it is also conceivable to use a device to emit or process ultrasound signals. A corresponding ultrasonic head would then be integrated into the catheter 2 together with a feed line. This is dealt with further below.

An additional ancillary unit provided for is a device 4 for emitting high-frequency current pulses, which are emitted to corresponding ablation electrodes in the region of the tip of the catheter in order to necrotize adjacent tissue if necessary.

Furthermore a device 5 is assigned, via which an ECG can be performed, for which suitable electrodes are likewise integrated into the tip of the catheter, which is described further below. Finally a device 6 is provided in the form of a position recording system, by means of which the position and/or orientation of the tip of the catheter inserted into the area under examination can be determined in the position recording coordinates system.

Furthermore a central control or processing device is provided, which in the example shown communicates with the device 3, the device 5 and the device 6. The control or processing device 7 thus for example receives the OCT data, i.e. image data obtained in optical coherence tomography, and processes it for example to produce an image which can be output on a monitor 8. Furthermore it is given the data from the device 5, consequently therefore continuously recorded ECG signal data. If the device 7 is designed for mapping on the basis of the ECG signals, it is possible that on the basis of the ECG signals a three-dimensional spatial image of the area under examination, for example of the heart, can be generated on the basis of the ECG signals, in which for example areas whose stimulus conduction has been disrupted are optically characterized, said areas being located on the basis of any discrepancies between the local ECG signals and signals from the environment. This image can also be reproduced on the monitor. In addition, for example, the OCT images and the ECG data are "married" with one another by the control or processing device 7. This means that the OCT image from the scanned area can be assigned to each ECG signal. Thus if an unambiguous pathological region is identified in the ECG mapping, the doctor can immediately view the assigned OCT image. Position recording using the position recording device 6 is expedient for this, since in this way a simple ECG mapping or simple coordinate recording and assignment of the coordinates to the respective signal package as well as to the respective OCT image is possible, so that both can be spatially referenced at any time. At this point it should be noted that devices 5 and 6 are optional; it is only necessary to perform the ECG if an area to be treated using ablation cannot be recorded and located purely optically, i.e. using the OCT image. This is the case for example with examinations in the heart relating to disruption of stimulus conduction which can result in an atrial flutter or similar, since the regions causing the flutter can be determined purely electrophysiologically, but not optically.

Furthermore an external computing unit 9 is provided, which can for example be a data processing or control device of a magnetic resonance system or of another examination procedure. This data processing device 9 can give the control or processing device 7 image data, for example a 3D image data record of this examination procedure. If for example the heart was previously recorded by means of an MR examination and a 3D data record was determined, it is now possible to give the control or processing device 7 this data record, so that it can output a 3D MR image, into which for example OCT images captured using corresponding position recording and registration of the position recording coordinates system of the device 6 can then be precisely inserted using the coordinates system on which the 3D MR image data is based. The same procedure is also possible with any ECG mapping image.

In the exemplary embodiment, FIG. 2 shows the tip 10 of a catheter of a first embodiment in detail. A thin optical fiber guide 11 is shown, via which the light on which OCT imaging is based is supplied, or the recorded reflected light is coupled out. The light is supplied and the decoupled light is processed using the device 3. A window 12 in the region of the tip of the catheter is provided for this purpose, from which the light is coupled out vertical to the longitudinal axis of the catheter. To this end the optical fiber guide 11 is designed accordingly, as is known. The decoupled light beam rotates, so that an annular image of the area adjacent to the tip is captured.

An ablation electrode 13 is further provided, which is fed via a power feed line 14. This enables adjacent tissue to be necrotized using high-frequency pulses of current.

Furthermore a plurality of electrodes 15 is provided, which are arranged on the outside of the catheter and can be controlled via a respective feed line 16 for derivation of ECG signals.

All three "work components", namely the OCT device, the ablation device and the ECG device can be operated simultaneously. This means it is possible, while ablation is ongoing, continuously to capture OCT images, to enable the ablation result to be recorded purely optically in situ. At the same time it is also possible, while ablation is ongoing or immediately thereafter while OCT imaging is ongoing, to perform an ECG using the electrodes 15, to determine whether stimulus conduction disruption has been improved as a result of ablation.

FIG. 3 shows another tip 17 of the catheter of a second embodiment. Here too an optical fiber 18 is provided, but it is a fiber bundle of many individual light guides rather than a single fiber. The light is coupled in and out via an OCT lens 19 arranged in the tip in the longitudinal direction of the catheter. Upstream of this is a collimator 28, which ensures that the light emitted by a fiber was reflected precisely to the one from which the light was emitted. This ensures that the OCT imaging is not impaired with this type of "longitudinal coupling in and out".

Otherwise electrodes 20 and the ablation device 21 are also provided, the latter being positioned laterally here. Different local positioning options are of course also conceivable here.

Finally FIG. 4 shows another tip 22 of the catheter. In this case, instead of an OCT imaging device an ultrasound device comprising an ultrasonic head 23 arranged in the tip with a corresponding signal line 24 is provided, via which ultrasound signals can be emitted and corresponding reflected signals recorded. These are given to the device 3 via the line 24.

Besides the electrodes 25 and the ablation device 26 a position sensor 27 is also provided here, comprising one or more individual sensors, and interworking with the device 6 of the position recording system and enabling the spatial position and orientation of the tip of the catheter to be recorded in the position recording coordinates system. Depending on how precisely the position/orientation is to be recorded, this can be a sensor enabling three spatial directions to be recorded, i.e. the x, y and z position. It is additionally also possible to record the three assigned rotation directions around the respective axes at the same time, in which case this would produce a 6D sensor.

Although the embodiments according to FIGS. 2 to 4 each show electrodes for ECG derivation, these are, as described, not absolutely essential, since the use of the electrodes or ECG derivation depends on which area of examination is being treated with the catheter. For example, if vessel malformations, tumors or similar are being treated in the course of the ablation with the catheter, these defects can be recorded purely optically and their nature, size and position can be recorded without further action via the imaging device, whether it is an OCT or an ultrasound device. The electrodes are primarily necessary only if the pathological area cannot be detected optically.

The invention claimed is:

1. A catheter device, comprising:
a catheter for inserting into an organ or vessel of a human or animal body, the catheter comprising:
an ablation device having an ablation electrode arranged at a tip of the catheter for applying ablation to organ tissue or vessel tissue using high-frequency currents;
an imaging device, fixedly arranged on the catheter, for recording an image of the organ tissue or the vessel tissue adjacent to the tip when the catheter is inserted;
an ECG device, fixedly arranged on the catheter, for recording an ECG, the ECG device comprising an ECG electrode for acquiring ECG signals arranged at the tip of the catheter;
a position detecting device comprising at least one position sensor arranged fixedly on the catheter near the catheter tip and a position signal receiver for detecting a current position or orientation of the catheter tip relative to a coordinate system of a three-dimensional spatial image generated on the basis of the ECG signals; and
a common control device operatively connected to the imaging device, the ECG device and the position detecting device,
wherein the ablation device, the ECG device and the imaging device are operatively connected to one another and configured to simultaneously apply the ablation, acquire the ECG signals, and record the image; and
the common control device is configured to correlate the recorded image, the acquired ECG signals, and the current position of the catheter tip, respectively with one another, for orientation of the catheter device.

2. The catheter device according to claim 1, wherein the catheter is an intravascular catheter.

3. The catheter device according to claim 1, wherein the imaging device is an ultrasound device.

4. The catheter device according to claim 1, wherein the imaging device is an optical coherence tomography device.

5. The catheter device according to claim 4, wherein the optical coherence tomography device includes one single light-conducting optical fiber.

6. The catheter device according to claim 1, wherein the ECG device is configured to generate an image display representing an examination area, the examination area limited by such organ tissue or vascular tissue providing the ECG signals.

7. The catheter device according to claim 4, wherein the optical coherence tomography device includes an optical fiber bundle comprising a plurality of individual optical fibers including a common collimator assigned to the optical fiber bundle.

* * * * *